(12) United States Patent
Li et al.

(10) Patent No.: US 10,015,992 B2
(45) Date of Patent: Jul. 10, 2018

(54) ATOMIZER AND ELECTRONIC CIGARETTE

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Xiaoqiang Zhao, Shenzhen (CN); Guiyuan Yu, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 0 days.

(21) Appl. No.: 15/407,230

(22) Filed: Jan. 16, 2017

(65) Prior Publication Data

US 2017/0202268 A1 Jul. 20, 2017

(30) Foreign Application Priority Data

Jan. 18, 2016 (CN) .................... 2016 2 0043887 U
Jan. 20, 2016 (CN) .................... 2016 2 0053006 U (51) Int. Cl.
*A24F 13/00* (2006.01)
*A24F 47/00* (2006.01)
*A24F 7/02* (2006.01)
*F16J 15/02* (2006.01)

(52) U.S. Cl.
CPC ............. *A24F 47/008* (2013.01); *A24F 7/02* (2013.01); *F16J 15/022* (2013.01)

(58) Field of Classification Search
CPC .................................................. A24F 47/008

USPC ................................. 131/173–330; 439/135
See application file for complete search history.

(56) References Cited

U.S. PATENT DOCUMENTS

| 8,563,859 | B1 * | 10/2013 | Baldwin | ............... H02G 3/14 174/53 |
| 2005/0191885 | A1 * | 9/2005 | Son | .................. H01R 13/447 439/135 |
| 2013/0319438 | A1 | 12/2013 | Liu | |
| 2014/0217056 | A1 | 8/2014 | Parekh et al. | |
| 2015/0250340 | A1 | 9/2015 | Liu et al. | |

(Continued)

FOREIGN PATENT DOCUMENTS

| CN | 203388273 U | 1/2014 |
| CN | 204409588 U | 6/2015 |

(Continued)

*Primary Examiner* — Phuong Dinh
(74) *Attorney, Agent, or Firm* — Cheng-Ju Chiang (57) ABSTRACT

An atomizer being combined with a power supply to form an electronic cigarette is disclosed. The atomizer comprises: a housing with a first end and a second end; a mouthpiece, connected to the first end of the housing, wherein the second end is connected to the power supply; a reservoir, formed in the housing and configured to contain tobacco liquid; and an atomizing element, configured to atomize the tobacco liquid to form aerosol; wherein an injecting hole and a vent hole are formed on the first end of the housing, the injecting hole and the vent hole are in communication with the reservoir, the atomizer further comprises a cover formed on the first end of the housing, and the cover is configured for exposing or covering the injecting hole and the vent hole. It is more conveniently to inject tobacco liquid for users.

20 Claims, 9 Drawing Sheets

(56) References Cited

U.S. PATENT DOCUMENTS

| | | |
|---|---|---|
| 2016/0192707 A1 | 7/2016 | Li et al. |
| 2016/0219935 A1 | 8/2016 | Qiu |
| 2016/0366944 A1* | 12/2016 | Larson .................. A24F 47/008 |
| 2017/0210520 A1* | 7/2017 | Woodward ............. B65D 50/00 |

FOREIGN PATENT DOCUMENTS

| | | |
|---|---|---|
| EP | 2614731 A1 | 7/2013 |
| EP | 3143884 A2 | 3/2017 |

* cited by examiner

ATOMIZER AND ELECTRONIC CIGARETTE

CROSS-REFERENCE OF RELATED APPLICATIONS

This application is based upon and claims the benefit of priority from the prior Chinese Patent Applications, Application No. 201620043887.7, filed on Jan. 18, 2016, and Application No. 201620053006.X, filed on Jan. 20, 2016, the entire contents of which are incorporated herein by reference.

FIELD OF THE DISCLOSURE

The present disclosure relates to the field of electronic cigarette, and more particularly, to an atomizer and an electronic cigarette with the atomizer.

BACKGROUND OF THE DISCLOURE

As the electronic cigarette has advantages of safe-usage, convenience, health and environmental protection, more and more people pay attention to the electronic cigarette which is the replacement of an ordinary cigarette. The electronic cigarette comprises an atomizer and a power supply component, an atomizing component and a liquid-storing component for storing the tobacco liquid are included in the atomizer, a vapor passage is arranged in the liquid-storing component, and the atomizing component further comprises a liquid-absorbing element and a heating element. The tobacco liquid in the liquid-absorbing element is atomized to form aerosol when the heating element heats, and then the aerosol flows through the vapor passage, thus an effect of a cigarette is achieved.

There are mainly two types of the atomizer in the prior art, which are a disposable atomizer and a refillable atomizer with tobacco liquid. The usage cost may be reduced, as the refillable atomizer can be recycled. Therefore, an atomizer, into which the tobacco liquid can be injected conveniently, is needed.

SUMMARY OF THE DISCLOSURE

An atomizer and an electronic cigarette are disclosed in the disclosure to inject tobacco liquid into the atomizer more conveniently.

In accordance with one aspect of the disclosure, an atomizer being combined with a power supply to form an electronic cigarette, is disclosed, comprises: a housing with a first end and a second end; a mouthpiece, connected to the first end of the housing, wherein the second end is connected to the power supply; a reservoir, formed in the housing and configured to contain tobacco liquid; and an atomizing element, configured to atomize the tobacco liquid to form aerosol; wherein an injecting hole and a vent hole are formed on the first end of the housing, the injecting hole and the vent hole are in communication with the reservoir, the atomizer further comprises a cover formed on the first end of the housing, and the cover is configured for exposing or covering the injecting hole and the vent hole.

Wherein, the first end of the housing is stepped, and the cover has a shape corresponding to a stepped location of the first end of the housing such that the cover is containable in the stepped location of the first end of the housing.

Wherein, the cover is rotatable in relative to the first end of the housing, to expose or cover the injecting hole and the vent hole.

Wherein, the atomizer further comprises a rotation shaft formed on the first end of the housing, and the cover is pivoted along the rotation shaft such that the cover is rotatable in relative to the first end of the housing.

Wherein, the cover is slidable with respect to the first end of the housing, to expose or cover the injecting hole and the vent hole.

Wherein, the first end of the housing is circular-shaped, and the cover is slidable along a radial direction of the first end of the housing.

Wherein, two sliding slots are formed on any one of the first end of the housing and the cover, two protruded guiding elements are formed on another of the first end of the housing and the cover, and the two protruded guiding elements are inserted into the two sliding slots respectively and slidable along the two sliding slots such that the cover is slidable along the radial direction of the first end of the housing.

Wherein, the two protruded guiding elements are fixedly formed on the first end of the housing or the cover via being inserted into two first fixed holes formed on the first end of the housing or the cover, respectively.

Wherein, further comprising: a positioning structure for hinting the first end of the housing is tightly closed by the cover; wherein the positioning structure comprises two deformation elements and two matching elements formed on the cover and the first end of the housing respectively, when a matching relation is formed between the two deformation elements and the two matching element, the stepped location of the first end of the housing is tightly closed by the cover; and when the matching relation is released, the cover exposes at least a part of the stepped location of the first end of the housing.

Wherein, the two deformation elements are fixedly formed on the cover or the first end of the housing via being inserted into two second fixed holes formed on the cover or the first end of the housing, respectively.

Wherein, the two deformation elements are elastic thimbles respectively, and the two matching elements are performed by the two sliding slots formed on the first end of the housing or the cover.

Wherein, each of the two deformation elements comprises a spring and a top element arranged on the spring.

Wherein, a seal ring is further arranged on the first end and around the injecting hole and the vent hole, for forming a sealing connection between the cover and the first end of the housing when the cover covers the injecting hole and the vent hole, to avoid the tobacco liquid leaking.

Wherein, a seal ring is further arranged on the cover and around the injecting hole and the vent hole, for forming a seal connection between the cover and the first end of the housing when the cover covers the injecting hole and the vent hole, to avoid the tobacco liquid leaking.

Wherein, the injecting hole has an aperture larger than that of the vent hole.

Wherein, a rugged portion is formed on the cover for enhancing a users' touch.

Wherein, the mouthpiece is detachably connected to the first end of the housing.

In accordance with another aspect of the disclosure, an electronic cigarette is disclosed, comprising: an atomizer; and a power supply, configured to supply electric power to the atomizer; wherein the atomizer comprises: a housing with a first end and a second end; a mouthpiece, connected to the first end of the housing, wherein the second end is connected to the power supply; a reservoir, formed in the housing and configured to contain tobacco liquid; and an atomizing element, configured to atomize the tobacco liquid to form aerosol; wherein an injecting hole and a vent hole are formed on the first end of the housing, the injecting hole and the vent hole are in communication with the reservoir, the atomizer further comprises a cover formed on the first end of the housing, and the cover is configured for exposing or covering the injecting hole and the vent hole.

Wherein, the cover is rotatable in relative to the first end of the housing, to expose or cover the injecting hole and the vent hole.

Wherein, the cover is slidable with respect to the first end of the housing, to expose or cover the injecting hole and the vent hole.

Beneficial effects of the disclosure may be as follows: the injecting hole and the vent hole are formed on the atomizer, which may be exposed or covered by the cover. Users may only move the cover to expose the injecting hole and the vent hole, when injecting tobacco liquid into the atomizer. Therefore, it is more convenient to operate.

BRIEF DESCRIPTION OF THE DRAWINGS

In order to better illustrate technical implementations of the disclosure, hereinafter the accompanying drawings used in embodiments will be described simply. Obviously, the drawings as described are only some embodiments. All other drawings shall be obtained by those of skill in the art based on those drawings without making inventive efforts. Herein.

DETAILED DESCRIPTION OF THE DISCLOSURE

Now technical implementations of the disclosure will be described in definite and comprehensive details with reference to the accompanying drawings. Obviously, the embodiments as described are only some but not all the embodiments of the disclosure. All other embodiments obtained by those of skill in the art based on the embodiments of the disclosure without making inventive efforts shall all fall in the protection of the disclosure.

An atomizer in accordance with a first embodiment will be described with reference to FIGS. 1 to 3 below.

Figure 1:
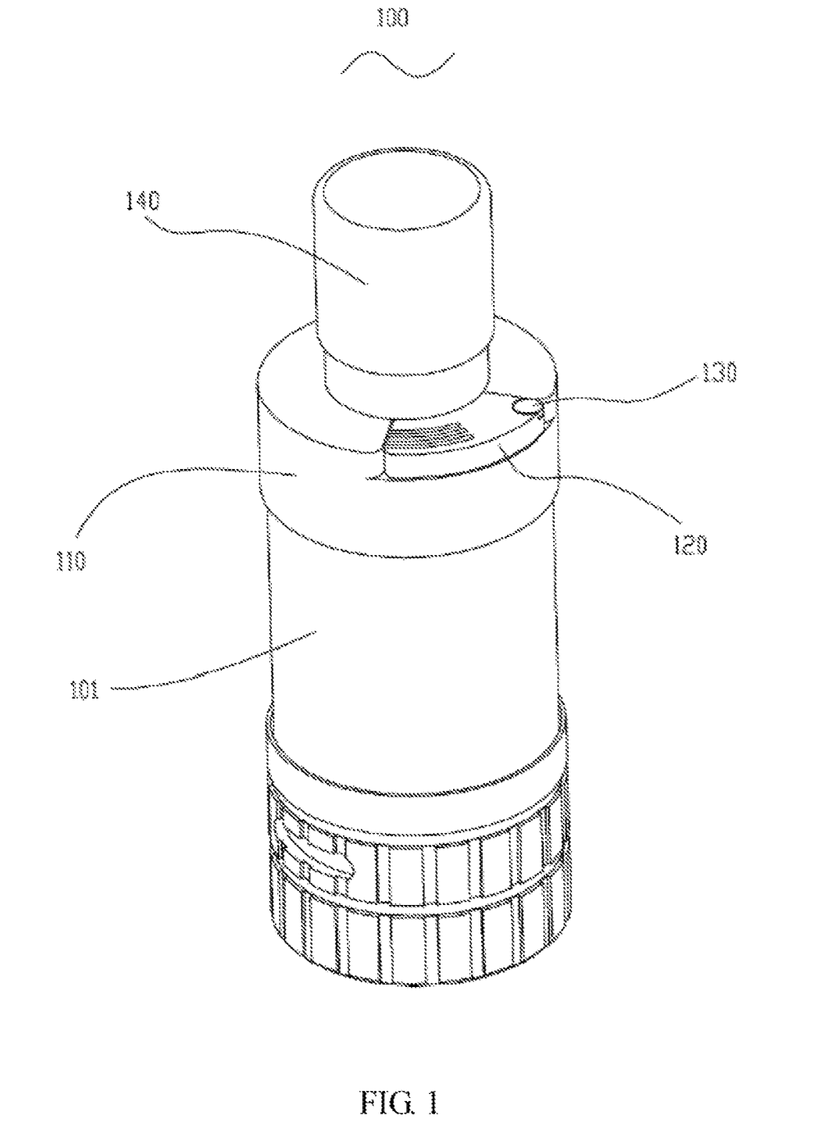
FIG. 1 is a structural view illustrating an atomizer in accordance with a first embodiment of the disclosure.
Figure 2:
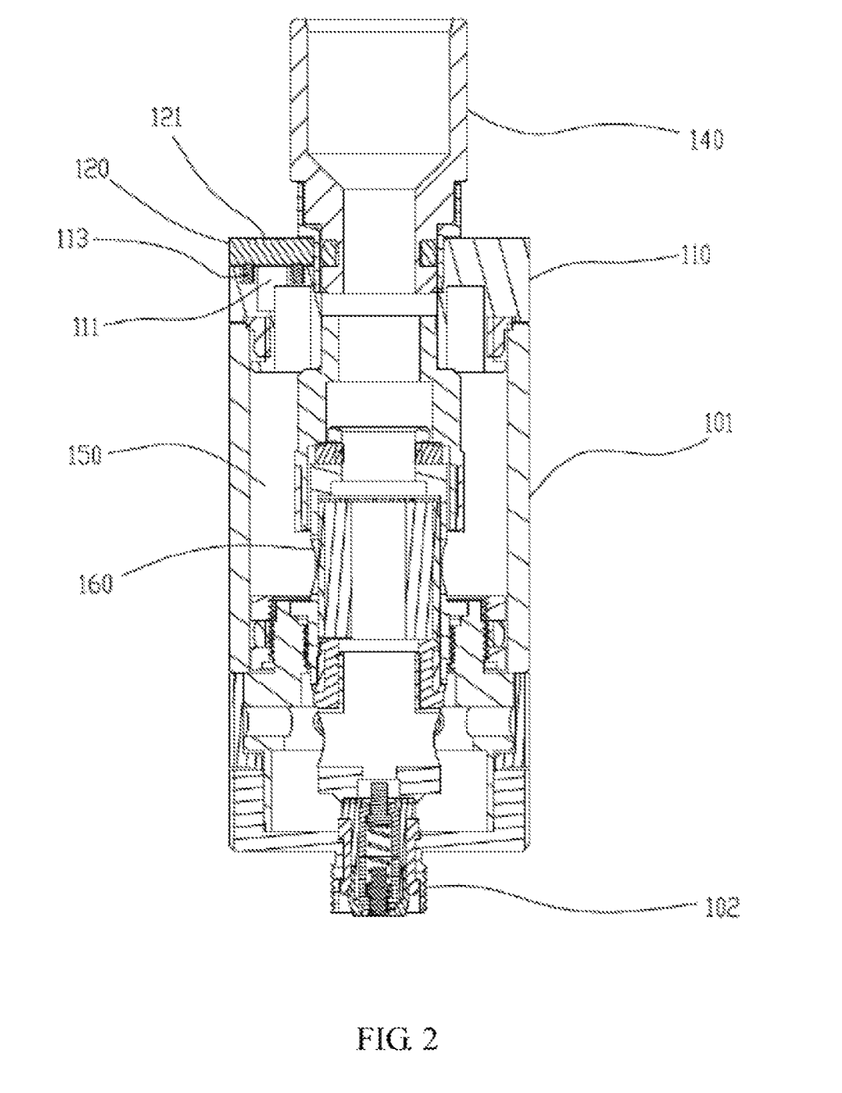
FIG. 2 is a schematic cutaway view of the atomizer in accordance with the first embodiment in FIG. 1.
Figure 3:
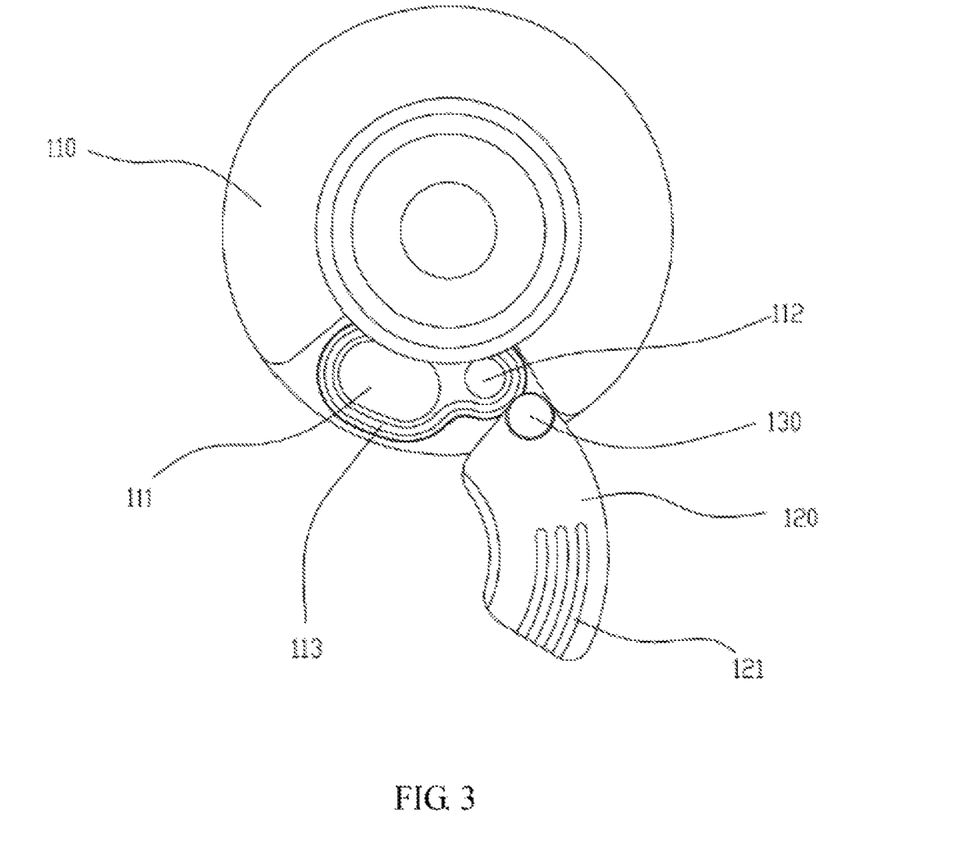
FIG. 3 is a top view of the atomizer in accordance with the first embodiment in FIG. 1.
Figure 4:
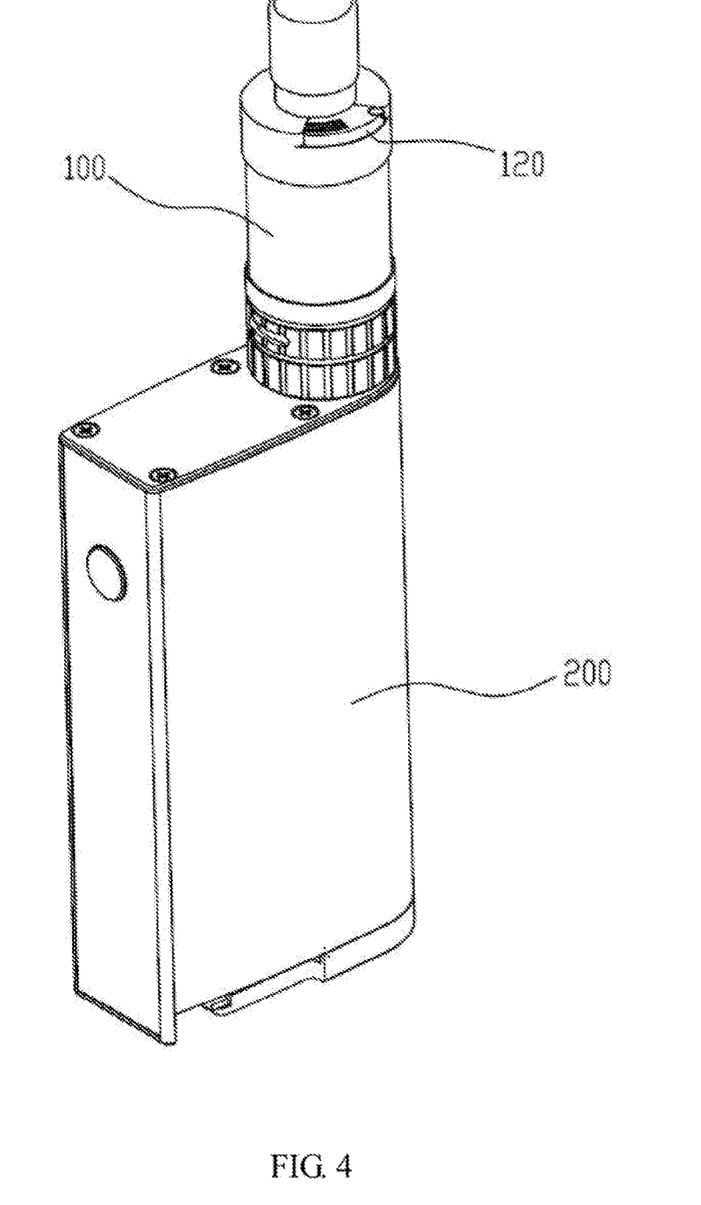
FIG. 4 is a structural view illustrating an electronic cigarette in accordance with a first embodiment of the disclosure.
Figure 5:
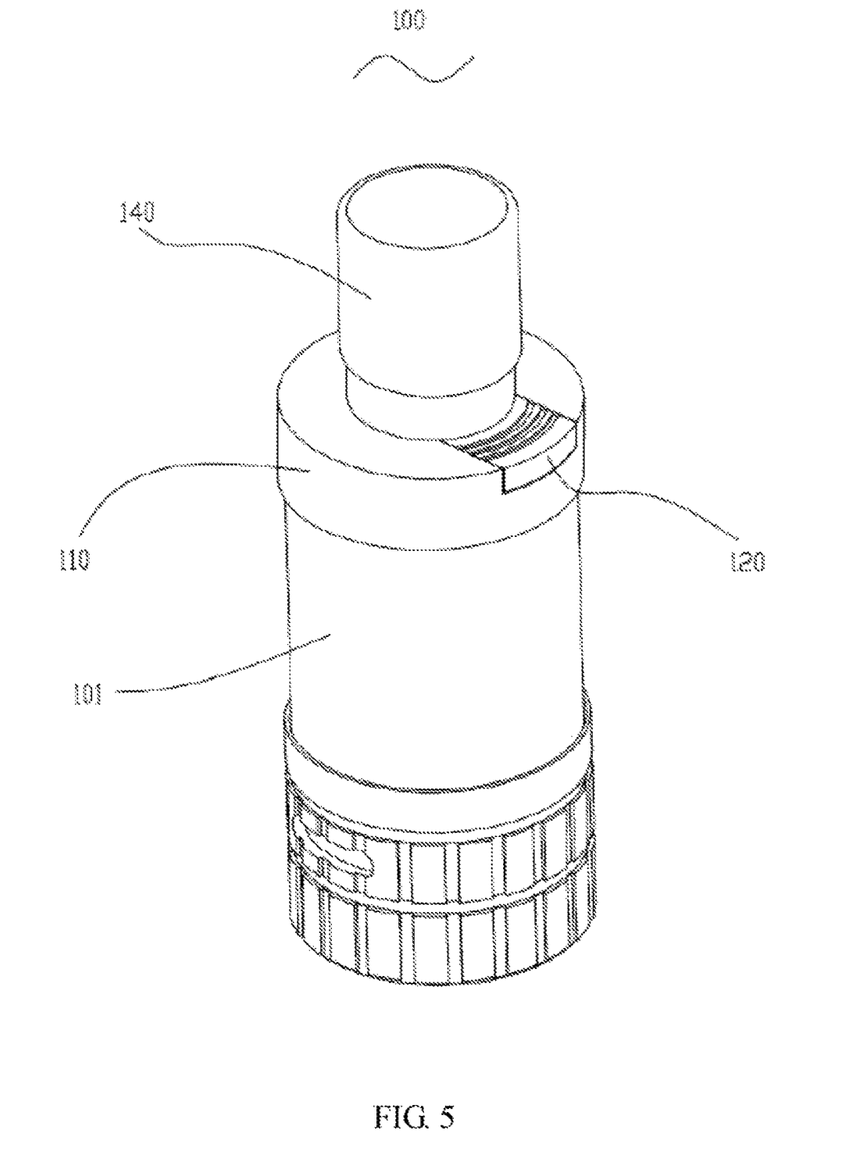
FIG. 5 is a structural view illustrating an atomizer in accordance with a second embodiment of the disclosure.
Figure 6:
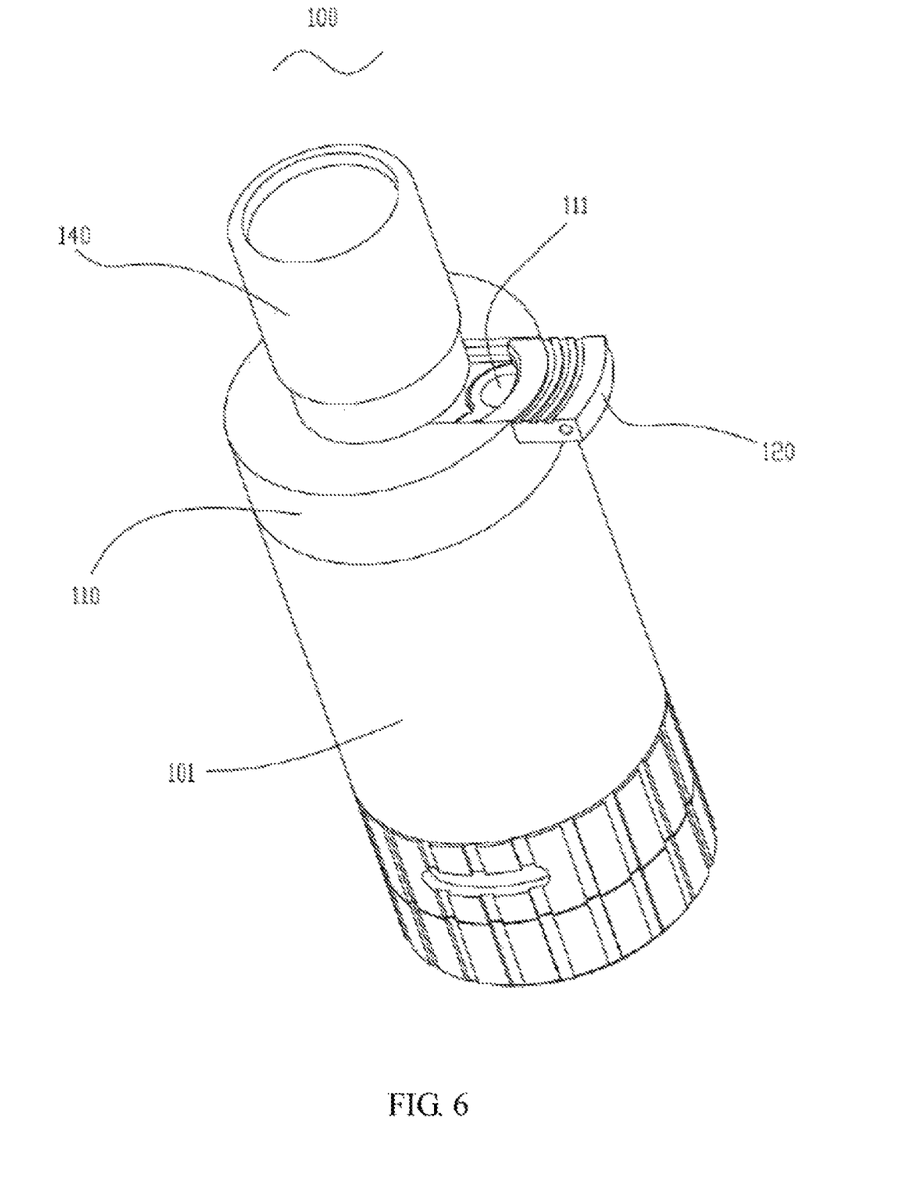
FIG. 6 is a structural view of the atomizer when a cover is opened in accordance with the second embodiment of the disclosure.
Figure 7:
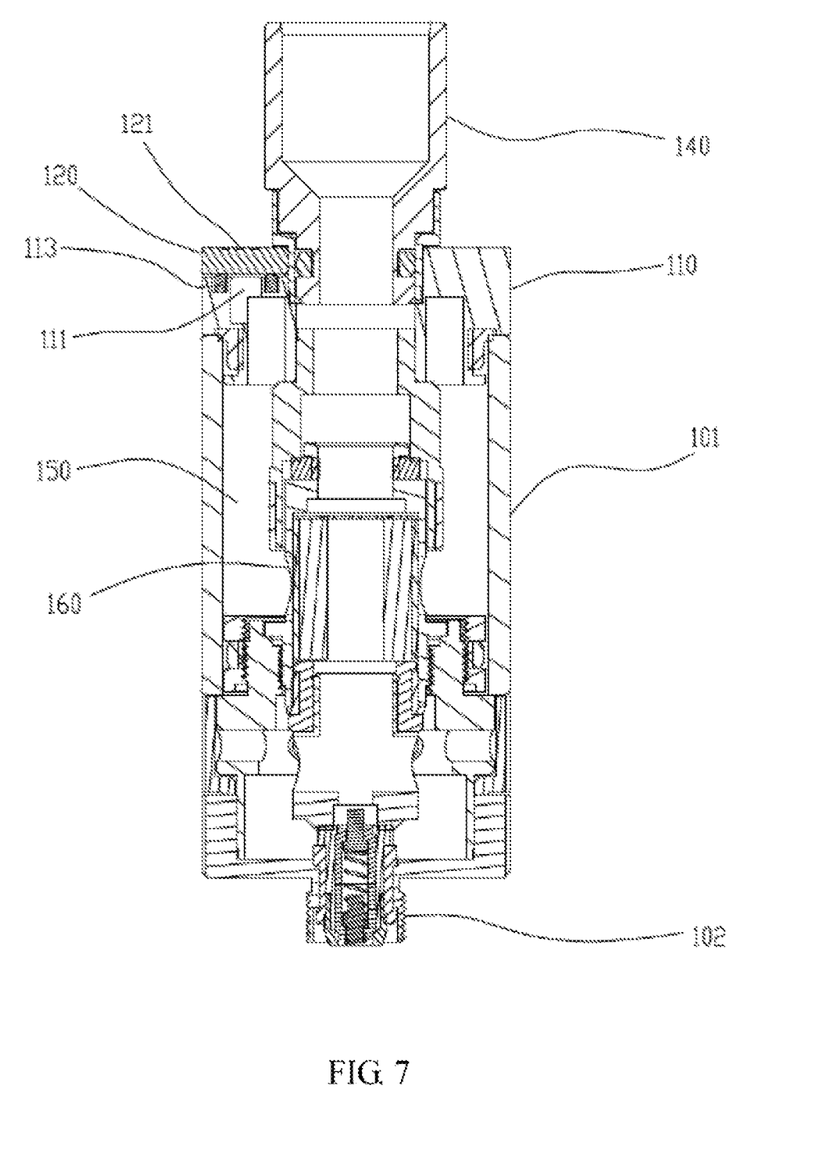
FIG. 7 is a schematic cutaway view of the atomizer in accordance with the second embodiment in FIG. 5.

Referring to FIGS. 1-3, the atomizer 100, which is combined with a power supply 200 (as shown in FIG. 4) to form an electronic cigarette, includes a housing 101 with a first end 110 and a second end 102, and a mouthpiece 140 connected to the first end 110 of the housing 101. A reservoir 150 configured to contain tobacco liquid and an atomizing element 160 configured to atomize the tobacco liquid to form aerosol are formed inner side of the housing 101. An injecting hole 111 and a vent hole 112 are formed on the first end 110, and the injecting hole 111 and the vent hole 112 are both communicated with the reservoir 150. A cover 120 is formed on the first end 110. The cover 120 is movable with respect to the first end 110 to expose and cover the injecting hole 110 and the vent hole 112. Further, the first end 110 is stepped, and the cover 120 has a shape corresponding to a stepped location of the first end 110 of the housing 101 such that the cover 120 is capable of being contained in the stepped location of the first end 110.

In the first embodiment, the cover 120 is rotatable in relative to the first end 110 to expose or cover the injecting hole 111 and the vent hole 112. Further, as shown FIG. 1 and FIG. 3, a rotation shaft 130 is formed on the first end 110, and the cover 120 is pivoted along the rotation shaft 130, thus the cover 120 may be rotatable in relative to the first end 110 to expose and cover the injecting hole 110 and the vent hole 112. Preferably, the rotation shaft 130 is formed near one edge of the stepped location of the first end 110 of the housing 101 where the vent hole 112 is formed, in this way, it is conveniently to inject tobacco liquid.

In the first embodiment, as shown in FIG. 2, the mouthpiece 140 is detachably connected to the first end 110. It is understood that the connection between the mouthpiece 140 and the first end 110 may also be in another manner, the mouthpiece 140 is fixed to the first end 110, for example in another embodiment.

As shown in FIGS. 2 and 3, a seal ring 113 is further arranged on the first end 110 and around the injecting hole 111 and the vent hole 112, which is configured to form a sealing connection between the cover 120 and the first end 110 when the cover 120 covers the injecting hole 111 and the vent hole 112 to avoid the tobacco liquid leaking. The seal ring 113 is made of rubber or silica gel material, in this way, a good sealing effect for the sealing connection between the cover 120 and the first end 110 may be achieved. Similarly, in another embodiment, the seal ring 113 may also be arranged on the cover 120. When the seal ring 113 is arranged on the cover 120, and around the injecting hole 111 and the vent hole 112. The seal ring 113 is configured to form a sealing connection between the cover 120 and the first end 110 when the cover 120 covers the injecting hole 111 and the vent hole 112 to avoid the tobacco liquid leaking.

Further, as shown in FIG. 3 again, the injecting hole 111 has an aperture larger than that of the vent hole 112.

As shown in FIGS. 2 and 3 again, a rugged portion 121 is further formed on the cover 120 for enhancing a users' touch. When opening the cover 120, the rugged portion 121 is helpful to enhance the touch between fingers and the cover 120.

As it can be seen, in the first embodiment, the injecting hole 111 and the vent hole 112 are formed on the atomizer 100, which are to be exposed or covered in an rotatable manner, therefore, users may only need to expose the injecting hole 111 and the vent hole 112 in the rotatable manner, when injecting tobacco liquid into the atomizer 100, thus it is more convenient to operate.

As shown in FIG. 4 which illustrates an electronic cigarette in accordance with a first embodiment of the disclosure, the electronic cigarette includes an atomizer 100 and a power supply 200. The atomizer 100 is connected to the power supply 200 through a detachable structure, such as a detachable threaded connection structure. The power supply 200 is configured to provide the atomizer 100 for electric power, and the atomizer 100 is one as described in the above first embodiment with reference to the accompanying FIGS. 1-3.

An atomizer in accordance with a second embodiment will be described with reference to FIGS. 5 to 8 below.

The difference between atomizers in the first embodiment and the second embodiment is that the cover 120 is slidable with respect to the first end 110 to expose or cover the injecting hole 111 and the vent hole 112. The remaining technical characteristics of the atomizer 100 in the second embodiment are same to those in the first embodiment, which are not to be described in details again here. Now the difference will be described in detail.

Figure 8:
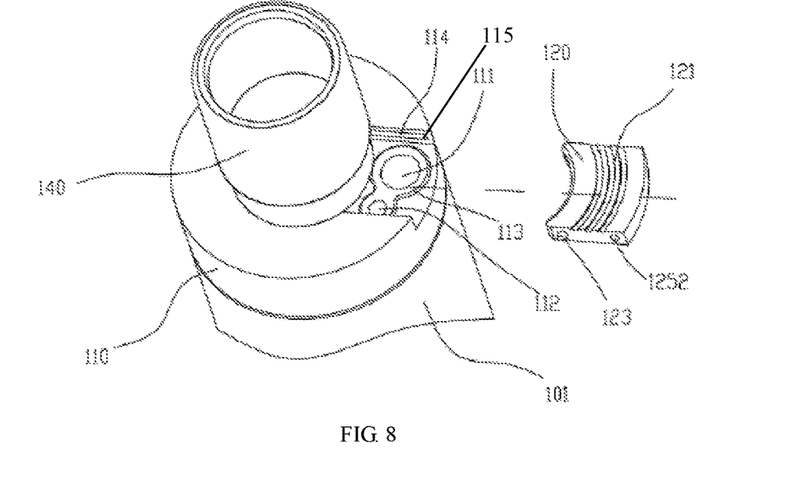
FIG. 8 is a partial structural view of the atomizer in accordance with the second embodiment in FIG. 5.

As shown in FIG. 8, in the second embodiment, the first end 110 is circular-shaped, and the cover 120 is slidable along a radial direction of the first end 110. Two sliding slots 114 is formed on the first end 110, and two guiding elements 123 are formed on both sides of the cover 120, respectively. The two guiding elements 123 are inserted into the two sliding slots 114 respectively and slidable along the two sliding slots 114 such that the cover 120 is slidable along the radial direction of the first end 110. The guiding element 123 is a cylindrical object. One end of one guiding element 123 is protruded at one side of the cover 120. One end of the other guiding element 123 is protruded at the other side of the cover 120. The guiding elements 123 are adapted to the sliding slots 114, and the guiding element 123 is always in the slide slot 114.

Further, two first fixed holes 122 are formed on the cover 120. The two guiding elements 123 are fixedly formed on the cover 120 via being inserted into the two first fixed holes 122, one ends of which are protruded from both sides of the cover 120, respectively. In this way, the guiding elements 123 are formed on the cover 120. What may be understood for the skilled in the art, the guiding element 123 may also be formed on the first end 110, and the slide slot 114 may also be formed on the cover 120. In this way, the two first fixed holes 122 are formed on the first end 110, and the two guiding elements 123 are fixedly formed on the first end 110 via being inserted into the two first fixed holes 122.

Figure 9:
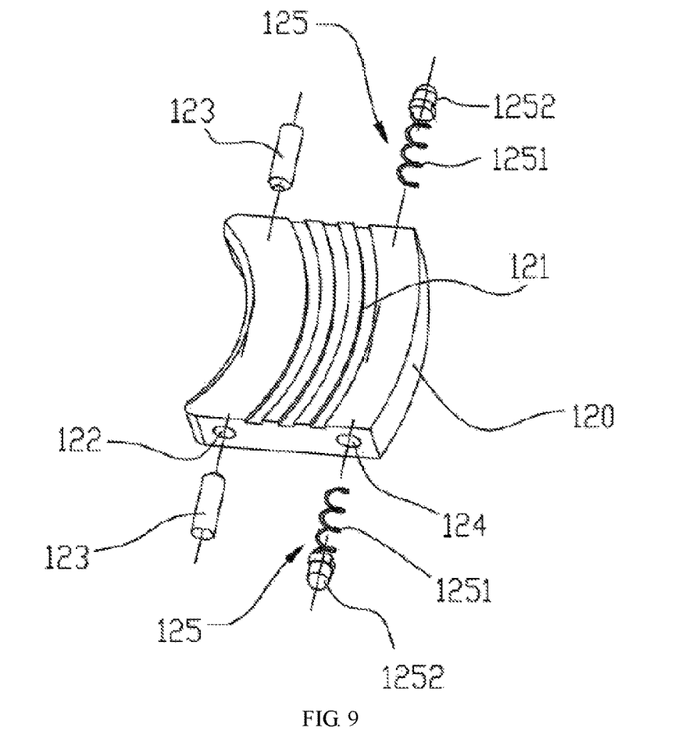
FIG. 9 is a disassembled view of a cover in accordance with the second embodiment in FIG. 5.

As shown in FIG. 9, the atomizer 100 further includes a positioning device for hinting the first end 110 is tightly closed by the cover 120. The positioning device includes two deformation elements 125 and two matching elements 115. The two deformation elements 125 are formed on the cover 120, and the two matching elements 115 are formed on the first end 110. When a matching relation is formed between the two deformation elements 125 and the two matching element 115, the stepped location of the first end 110 is tightly closed by the cover 120; and when the matching relation is released, the cover 120 exposes at least a part of the stepped location of the first end 110.

Further, two second fixed holes 124 are formed on the cover 120. The two deformation elements 125 are fixedly formed on the cover 120 via being inserted into two second fixed holes 124 formed on the cover 120. In this way, the deformation elements 125 are formed on the cover 120. What may be understood for the skilled in the art, the deformation elements 125 may also be formed on the first end 110. In this way, the two second fixed holes 124 are formed on the first end 110, and the two deformation elements 125 are fixedly formed on the first end 110 via being inserted into the two second fixed holes 124.

In the second embodiment, the two deformation elements 125 are elastic thimbles respectively, and the matching elements 115 are performed by the two sliding slots 114 formed on the first end 110. The elastic thimbles are matched with the two sliding slots 114, respectively. It should be state that the matching element 115 and the slide slot 114 are integrated in this embodiment, thus the deformation element 125 is matched with the slide slot 114. What may be understood the matching element 115 and the slide slot 114 may also be formed separately.

The elastic thimble includes a top element 1252 and a spring 1251. The top element 1252 is arranged on the spring 1251. The top element 1252 is abutted against the slot when the first end 110 is tightly closed by cover 120.

As it can be seen, in the second embodiment, the injecting hole 111 and the vent hole 112 are formed on the atomizer 100, to be exposed or covered in a slidable manner, therefore, users may only need to expose the injecting hole 111 and the vent hole 112 through sliding the cover 120, when injecting tobacco liquid into the atomizer 100, thus it is more convenient to operate.

Figure 10:
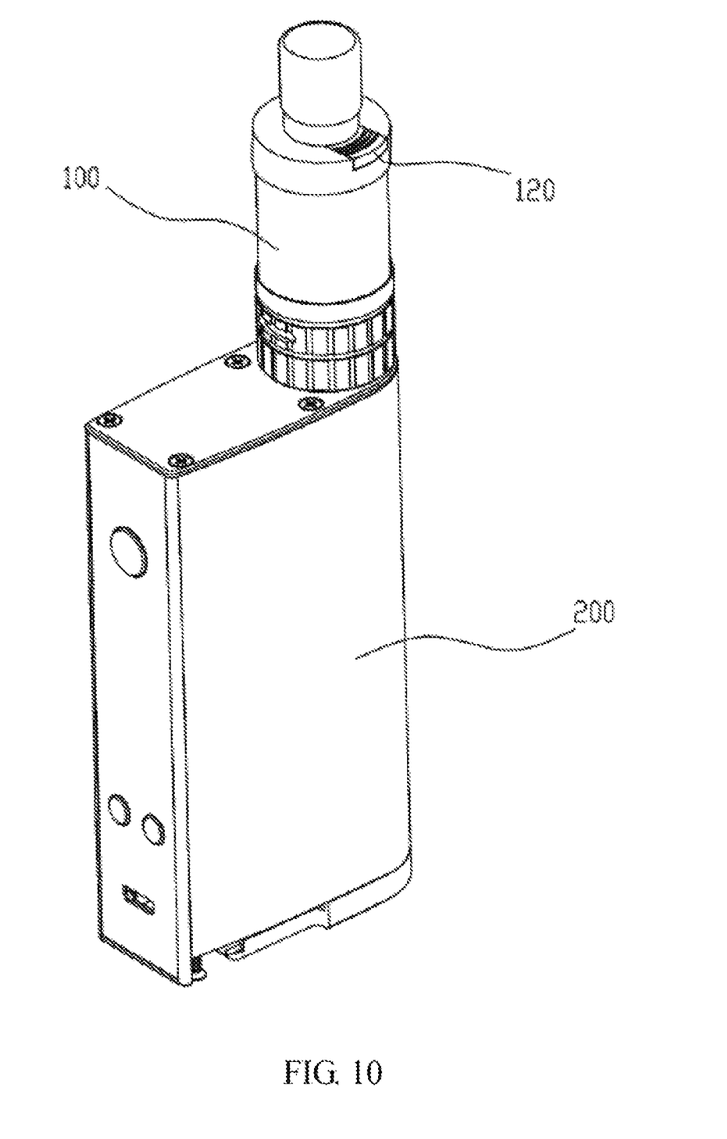
FIG. 10 is a structural view illustrating an electronic cigarette in accordance with a second embodiment of the disclosure.

As shown in FIG. 10 which illustrates an electronic cigarette in accordance with a second embodiment of the disclosure, the electronic cigarette includes an atomizer 100 and a power supply 200. The atomizer 100 is connected to the power supply 200 through a detachable structure, such as a detachable threaded connection structure. The power supply 200 is configured to provide the atomizer 100 for electric power, and the atomizer 100 is one as described in the above second embodiment with reference to the accompanying FIGS. 5-8.

In conclusion, the injecting hole and the vent hole are formed on the atomizer, which may be exposed or covered by the cover. Users may only move the cover to expose the injecting hole and the vent hole, when injecting tobacco liquid into the atomizer 100. Therefore, it is more convenient to operate.

The above as mentioned is about merely some embodiments of the disclosure, and not restrictive to the scope of the disclosure hereafter. Any equivalent structure or flow transformations made to the disclosure with the specification and drawings of the disclosure, or any direct or indirect applications of the disclosure on other related fields, shall all be covered within the protection of the disclosure.

What is claimed is:

1. An atomizer, being combined with a power supply to form an electronic cigarette, comprising:
    a housing with a first end and a second end;
    a mouthpiece, connected to the first end of the housing, wherein the second end is connected to the power supply;
    a reservoir, formed in the housing and configured to contain tobacco liquid; and
    an atomizing element, configured to atomize the tobacco liquid to form aerosol;
    wherein an injecting hole and a vent hole are formed on the first end of the housing, the injecting hole and the vent hole are in communication with the reservoir, the atomizer further comprises a cover formed on the first end of the housing, and the cover is configured for exposing or covering the injecting hole and the vent hole.

2. The atomizer according to claim 1, wherein the first end of the housing is stepped, and the cover has a shape corresponding to a stepped location of the first end of the housing such that the cover is capable of being contained in the stepped location of the first end of the housing.

3. The atomizer according to claim 2, wherein the cover is rotatable in relative to the first end of the housing, to expose or cover the injecting hole and the vent hole.

4. The atomizer according to claim 3, wherein the atomizer further comprises a rotation shaft formed on the first end of the housing, and the cover is pivoted along the rotation shaft such that the cover is rotatable in relative to the first end of the housing.

5. The atomizer according to claim 2, wherein the cover is slidable with respect to the first end of the housing, to expose or cover the injecting hole and the vent hole.

6. The atomizer according to claim 5, wherein the first end of the housing is circular-shaped, and the cover is slidable along a radial direction of the first end of the housing.

7. The atomizer according to claim 6, wherein two sliding slots are formed on any one of the first end of the housing and the cover, two protruded guiding elements are formed on another of the first end of the housing and the cover, and the two protruded guiding elements are inserted into the two sliding slots respectively and slidable along the two sliding slots such that the cover is slidable along the radial direction of the first end of the housing.

8. The atomizer according to claim 7, wherein the two protruded guiding elements are fixedly formed on the first end of the housing or the cover via being inserted into two first fixed holes formed on the first end of the housing or the cover, respectively.

9. The atomizer according to claim 5, further comprising:
a positioning structure for hinting the first end of the housing is tightly closed by the cover;
wherein the positioning structure comprises two deformation elements and two matching elements formed on the cover and the first end of the housing respectively, when a matching relation is formed between the two deformation elements and the two matching element, the stepped location of the first end of the housing is tightly closed by the cover; and when the matching relation is released, the cover exposes at least a part of the stepped location of the first end of the housing.

10. The atomizer according to claim 9, wherein the two deformation elements are fixedly formed on the cover or the first end of the housing via being inserted into two second fixed holes formed on the cover or the first end of the housing, respectively.

11. The atomizer according to claim 10, wherein the two deformation elements are elastic thimbles respectively, and the two matching elements are performed by the two sliding slots formed on the first end of the housing or the cover.

12. The atomizer according to claim 11, wherein each of the two deformation elements comprises a spring and a top element arranged on the spring.

13. The atomizer according to claim 1, wherein a seal ring is further arranged on the first end and around the injecting hole and the vent hole, for forming a sealing connection between the cover and the first end of the housing when the cover covers the injecting hole and the vent hole, to avoid the tobacco liquid leaking.

14. The atomizer according to claim 1, wherein a seal ring is further arranged on the cover and around the injecting hole and the vent hole, for forming a seal connection between the cover and the first end of the housing when the cover covers the injecting hole and the vent hole, to avoid the tobacco liquid leaking.

15. The atomizer according to claim 1, wherein the injecting hole has an aperture larger than that of the vent hole.

16. The atomizer according to claim 1, wherein a rugged portion is formed on the cover for enhancing a users' touch.

17. The atomizer according to claim 1, wherein the mouthpiece is detachably connected to the first end of the housing.

18. An electronic cigarette, comprising:
an atomizer; and
a power supply, configured to supply electric power to the atomizer;
wherein the atomizer comprises:
a housing with a first end and a second end;
a mouthpiece, connected to the first end of the housing, wherein the second end is connected to the power supply;
a reservoir, formed in the housing and configured to contain tobacco liquid; and
an atomizing element, configured to atomize the tobacco liquid to form aerosol;
wherein an injecting hole and a vent hole are formed on the first end of the housing, the injecting hole and the vent hole are in communication with the reservoir, the atomizer further comprises a cover formed on the first end of the housing, and the cover is configured for exposing or covering the injecting hole and the vent hole.

19. The electronic cigarette according to claim 18, wherein the cover is rotatable in relative to the first end of the housing, to expose or cover the injecting hole and the vent hole.

20. The electronic cigarette according to claim 18, wherein the cover is slidable with respect to the first end of the housing, to expose or cover the injecting hole and the vent hole.

* * * * *